United States Patent [19]
Seligman

[11] Patent Number: 5,991,664
[45] Date of Patent: Nov. 23, 1999

[54] COMPACT INDUCTIVE ARRANGEMENT FOR MEDICAL IMPLANT DATA AND POWER TRANSFER

[75] Inventor: Peter Seligman, Essendon, Australia

[73] Assignee: Cochlear Limited, Lane Cove, Australia

[21] Appl. No.: 09/012,908

[22] Filed: Jan. 23, 1998

[30] Foreign Application Priority Data

Mar. 9, 1997 [WO] WIPO .................. PCT/AU97/00566

[51] Int. Cl.[6] .................. A61N 1/02; A61N 1/36
[52] U.S. Cl. .................. 607/60; 607/61; 607/55
[58] Field of Search .................. 607/55–57, 60, 607/61

[56] References Cited

U.S. PATENT DOCUMENTS

| | | |
|---|---|---|
| 4,352,960 | 10/1982 | Dormer et al. .................. 607/57 |
| 4,932,405 | 6/1990 | Peeters et al. . | |
| 5,069,210 | 12/1991 | Jeutter et al. .................. 607/57 |
| 5,117,825 | 6/1992 | Grevious . | |
| 5,697,958 | 12/1997 | Paul et al. . | |
| 5,735,887 | 4/1998 | Barreras, Sr. et al. .................. 607/60 |
| 5,814,089 | 9/1998 | Stokes et al. . | |

OTHER PUBLICATIONS

"Energizing Implantable Transmitters By Means Of Coupled Inductance Coils", Kadefors et al, p. 177–183 177, vol. BME–16, No. 3.

Primary Examiner—William E. Kamm
Assistant Examiner—Carl H. Layno
Attorney, Agent, or Firm—Gottlieb, Rackman & Reisman, P.C.

[57] ABSTRACT

A system for providing transdermal communication with, and power to, a subcutaneously implanted device, for example the stimulator unit of a cochlear implant, by means of pairs of orthogonally wound, inductively coupled coils. The system provides a compact coil arrangement particularly suited to behind the ear and in-the ear multi-channel cochlear implants.

20 Claims, 3 Drawing Sheets

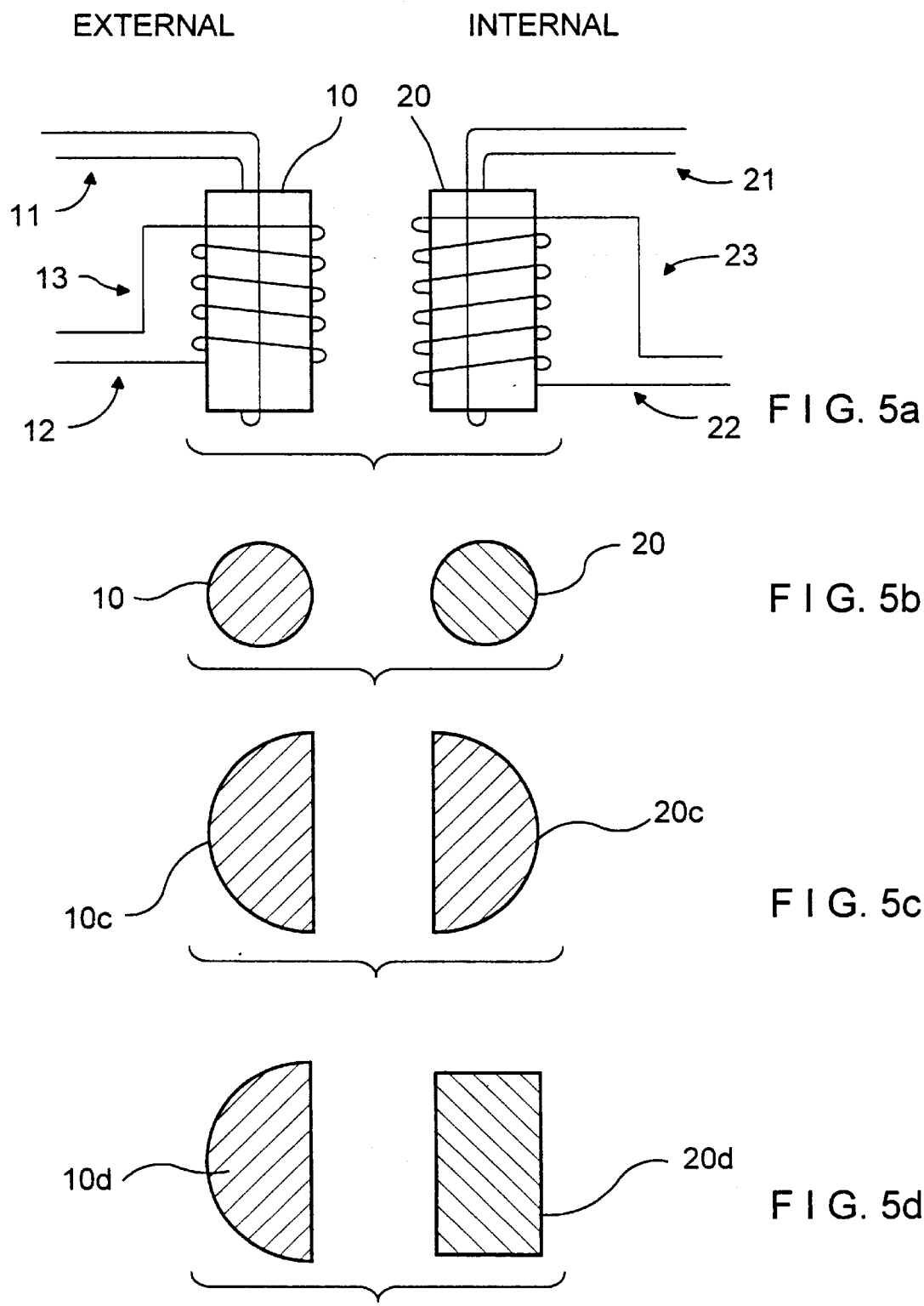

COMPACT INDUCTIVE ARRANGEMENT FOR MEDICAL IMPLANT DATA AND POWER TRANSFER

BACKGROUND OF THE INVENTION

1. Field of the Invention

The present invention relates to the construction and location of inductive links for implanted electrical devices, particularly but not exclusively cochlear prostheses.

2. Description of the Prior Art

A transdermal inductive link is commonly used to communicate power and data to implanted devices such as multi-channel cochlear implants. An internal coil is implanted with the device, and an external coil is positioned adjacent to it externally. In cochlear prostheses, it is common to locate the inductive components on the side of the head adjacent the mastoid bone, above and behind the pinna or outer ear. Other positions on the body have also been used, for locating transdermal links for instance on the chest. The inductive coils used are circular or open loops, and typically have a diameter of several centimeters. The external coil is connected to the speech processor via a cable.

In U.S. Pat. No. 4,932,405 there is described a cochlear implant system in which power is transmitted from an external processor and transmitter to an implanted receiver/stimulator by means of an inductive coil inserted into the ear canal. However, the disclosed system requires that data communication between the external and internal devices be carried out by means of a separate, preferably infra-red, communication channel which makes the transcutaneous crossing at a point some distance from the coil. Furthermore the inductive coil used for receiving the transmitted energy is to be implanted around the auditory duct which is a far from straightforward procedure.

In a paper, "Energizing Implantable Transmitters by means of Coupled Inductance Coils", Kadefors et al, p177–183 177, Vol BME-16, No 3, (July 1969) of IEEE Transactions on Bio-Medical Engineering, the authors discuss the use of ferrite cores to increase the efficiency of inductive transfer to implanted devices however the paper is concerned with only the transmission of power to an implanted circuit not with the more complex problem of supplying both power and data.

In recent years, there has been a trend to miniaturise the speech processor to the extent that it can be mounted behind the pinna. This miniaturisation has however not extended to the coil, which is still separate from the speech processor, connected to it by a cable, and usually mounted some distance above and behind the pinna.

The separate connection of the speech processor to the coil by a cable gives rise to a number of practical difficulties. It is not aesthetically pleasing, and the resulting effect on their appearance is of considerable concern to patients. A further difficulty is that the connecting cable is prone to breakage, and is accordingly a source of unreliability within the system.

An object of this invention is to provide an inductive arrangement of reduced size, so as to enable the elimination of the separate coil and processor arrangement and the cable that connects them.

A further object of the invention is to provide an inductive arrangement of reduced size which can facilitate transmission of both power and data.

SUMMARY OF THE INVENTION

According to one aspect the present invention provides an arrangement for transdermal inductive linking, comprising a first external inductor and a second implanted inductor, characterised in that each said inductor includes a ferromagnetic core, a first coil adapted for inductive transmission/reception at a first frequency, and a second coil adapted for inductive transmission/reception at a second frequency.

Preferably, the first and second coils are wound so as to be substantially orthogonal.

This arrangement enables a much more compact inductive system, and allows for a reduction in size of the internal and external inductive components.

According to another aspect, the present invention relates to an improved cochlear stimulation system, of the type comprising an implanted device, an external processing unit, a first external inductor and a second implanted inductor, characterised in that each said inductor includes a ferromagnetic core, a first coil adapted for inductive transmission/reception at a first frequency, and a second coil adapted for inductive transmission/reception at a second frequency.

Preferably, the inductor associated with the receiver stimulator unit is substantially integral with the receiver stimulator unit.

Preferably, the integral receiver stimulator unit and external inductive coil is adapted to be placed behind the pinna.

Preferably, the first and second coils are wound so as to be substantially orthogonal.

BRIEF DESCRIPTION OF DRAWINGS

The invention will now be described in more detail with reference to the accompanying figures, in which;

FIG. 5a is a somewhat diagrammatical side elevational veiw of the two internal and external inductors;

FIG. 5b shows a cross-sectional view of a first embodiment of the two coil cores of FIG. 5a.

FIG. 5c shows a cross-sectional view of a second embodiment of the two coil cores of FIG. 5a.

FIG. 5d shows a cross-sectional view of a third embodiment of the two coil cores of FIG. 5a.

DETAILED DESCRIPTION OF THE INVENTION

Figure 1:
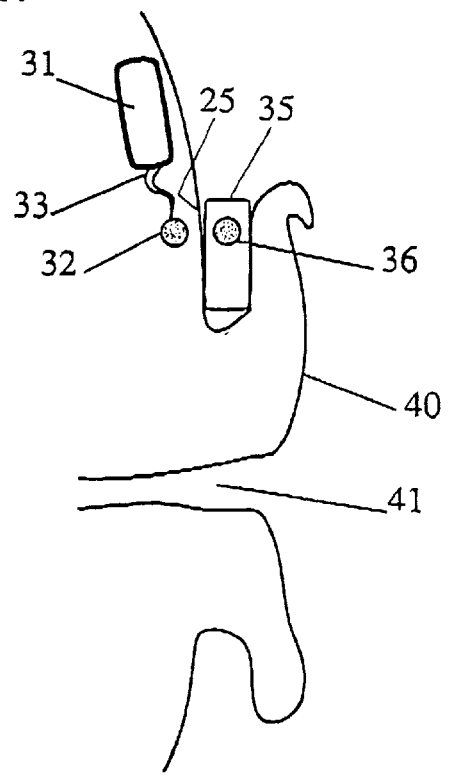
FIG. 1 illustrates, partly in section, appropriate placement of the combined receiver stimulator unit and coils and combined inductive coils and behind-the-ear processor.

It will be understood that the embodiment of the present invention described below is intended to be illustrative, and alternative implementations are possible within the scope of the inventive concept. The invention will be described in the context of a cochlear implant—however, it will be understood that the principles of the present invention are equally applicable to other implanted devices. Referring to FIG. 1, the principle of the present invention is to provide a first inductor 36 associated with the external speech processor 35 on one side of the skin barrier 25, and a second inductor 32 associated with the implanted device 31, arranged so that in use the cores of the coils are substantially parallel, and as near adjacent as possible. Each inductor has a ferromagnetic core, for example formed from ferrite. This can be seen more clearly from FIG. 2.

The use of such a coil enables a much more compact inductive component, thereby substantially reducing the dimensions of the external device in particular. It will be appreciated that the better the alignment between the cores, and the closer their spacing, the more efficient the coupling will be.

Figure 2:
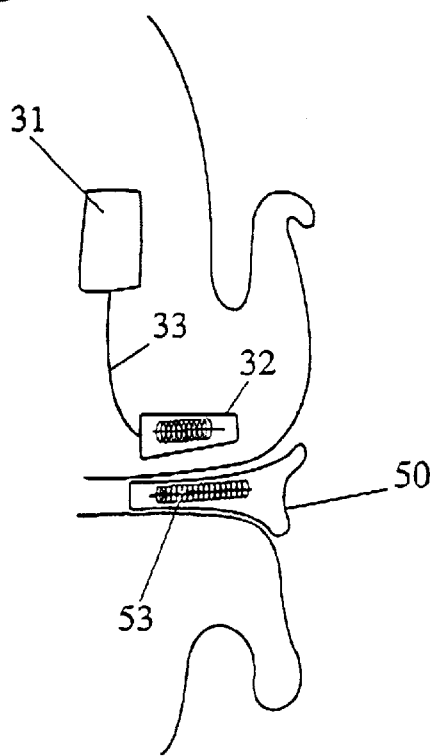
FIG. 2 illustrates, partly in section, another placement of the combined receiver stimulator unit and the combined in-the-ear speech processor and inductive coils.
Figure 3:
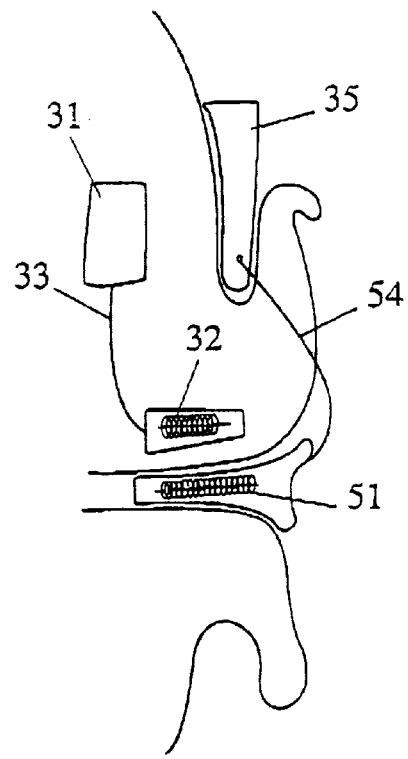
FIG. 3 illustrates, partly in section the placement of an in-the-ear inductive coil connected by a cable to a behind-the-ear speech processor and the placement of the implanted combined receiver stimulator unit and coil.

Utilising the coil with core arrangement allows for a much more compact coupling, which facilitates the coupling coil being placed within or adjacent to a speech processor unit, which can then be placed behind the pinna. This is shown in FIGS. 2 and 3. Speech processor unit 35 incorporates transmitter, or external, coil 36. The receiver, or internal, coil 32 is connected by lead 33 to the implanted electronics package 31. The relationship between the devices and the pinna 40 and ear canal 41 is apparent from the figures—the entire speech processor 35 and associated coil 36 may be positioned behind the ear. The precise operation and purposes of the speech processor unit and implanted electronics package does not form part of the present invention—it is the inductive link with which we are concerned. The coil may be placed in a number of possible positions—of course, the appropriate placement is determined by the underlying implanted coil.

It will be appreciated that whilst it is desirable that the external coil 36 is integral with the speech processor unit 35, this is not essential and these components could be connected by a lead.

Similarly, the implanted coil may be integral with the electronic unit, or could be connected by an implanted lead.

The external coil may be attached via a hinged or universal joint so that it can be readily aligned with the implanted coil. Alternatively, it could be attached to or formed within a moulding associated with the speech processor. A further variation upon the present invention would be to make the inductive link integral with a behind the ear microphone, such as is commonly used. In this arrangement, it would be still separate from the speech processor and require a connecting cable. However, it would obviate the need for the relatively large coil of conventional type, and associated lead.

Referring now to FIG. 2 there is depicted an in-the-ear cochlear prosthesis which instead of using a behind-the-ear speech processor makes use of integrated coils 53, according to the present invention, and speech processor 50, which fit into the external ear canal. An advantage of this arrangement is that the distance between the implanted coils 32, which are located in the mastoid cavity, and the external coils 53 is reduced thereby increasing coupling efficiency and reducing power consumption. The configuration of the coils is such that the two cores are substantially parallel as in the earlier embodiments. In the interests of hygiene the in-the-ear speech processor and coil should not completely occlude the ear canal.

It will be realised that this arrangement was not hitherto possible as prior art transcutaneous inductive links for multi-channel cochlear implants relied on coils of too large a diameter to allow placement in the ear canal.

A combination of the in-the-ear and behind the ear approaches to placement is shown in FIG. 3 wherein there is depicted a behind-the-ear speech processor 35 connected to a separate in-the-ear coil 51 by means of a cable 53. Such an arrangement suffers the disadvantage of requiring a cable connection between the speech processor and the in-the-ear coils however it enjoys the advantage of close intercoil coupling between the implanted 32 and in-the-ear coils while not having to meet the level of miniaturisation required for in-the-ear placement.

Figure 4:
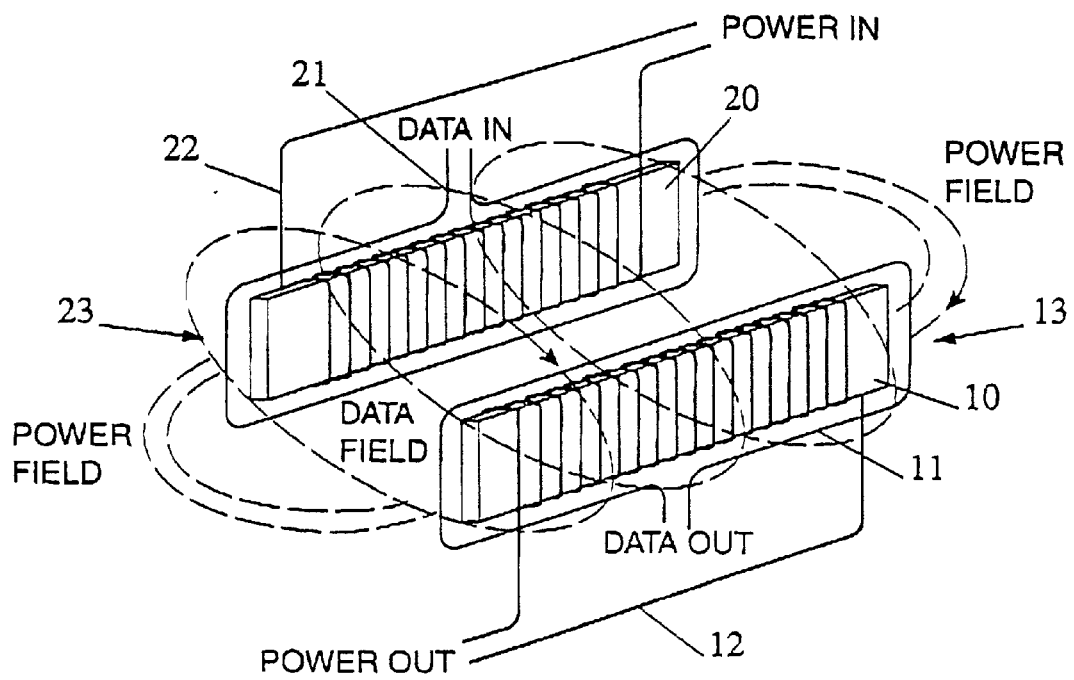
FIG. 4 illustrates schematically an orthogonal coil implementation according to the present invention.

A preferred implementation of the coils according to the invention is shown in FIG. 4. External inductor 13 and internal inductor 23 include respective ferrite cores 10, 20; a data winding 11, 21; and a power winding 12, 22. Thus, each inductor includes a coil specifically for data transfer, and an orthogonally wound coil for power transfer. This enables the use of different frequencies for power and data transfer, without requiring separate cores. A particular advantage of such an arrangement is that the optimal frequency range for power transfer is below 1 MHz, while it is desirable for data transfer to take place at a much higher frequency of over 5 MHz. This implementation allows for the use of separate frequencies for power and data transfer within a single inductor. In the illustrated arrangement, the magnetic field for power transfer can be arranged for maximum efficiency. Since efficiency is not crucial for data transfer, the relatively poor coupling of the data coils is not a disadvantage. As the coils are substantially orthogonal, the data and power fields do not interfere with each other.

While it is usually the case that the data transmission will consist of a baseband signal modulated onto a carrier, in some situations it may be desirable, and suitable, to simply couple the baseband data signal between the internal and external devices by means of one pair of parallel coils whilst power is transferred, as previously described, via the second pair.

As an example the external inductor 13 and internal inductor 23 may be implemented according to the following specifications. The core may be a ferrite rod 20 mm long and 1.5 mm in diameter. The power winding has 70 turns in a single layer. The data winding has 8 turns (orthogonal to power winding.

Alternatively it may be preferable to use other shapes, for example a rectangular prism (as shown in FIG. 4) so as to maximise the ferrite volume without increasing the mean spacing. Another configuration which has shown favourable results has been to use cores with semi-circular cross sections. Such a shape maximises the amount of ferrite in close proximity between the two cores. Furthermore, the two cores need not be the same shape as each other. In particular it may be preferable for the implanted core to be shorter and squatter (typically 6 mm long times 6 mm diameter) compared to the external core, so as to minimise the thickness of the implanted components.

These features of the invention are shown in FIGS. 5a–5d. FIG. 5a shows an elevational view of external inductor 13 comprising a core 10 and two orthogonal coils 11 and 12, and internal inductor 23 comprising a core 20 and two orthogonal coils 21 and 22. As seen in FIG. 5a, the core 20 of the internal inductor 23 is shorter than the core 10 of external inductor 10. FIG. 5b shows cores 10a and 20a having a circular cross section, thereby rendering these cores cylindrical. FIG. 5c shows cores 10b and 20b having a semicircular cross-section. FIG. 5d illustrates two cores 10d, 20d having different cross-sections. For example, core 10d may have a semicircular cross-section and core 20d may have a rectangular cross-section.

Whilst the present invention has been described in the context of a cochlear implant, it will be appreciated the same principle of size reduction will find application in many other implanted devices. Variations and additions to the invention are possible within the scope of the general inventive concept, as will be understood by those skilled in the art.

I claim:

1. A system for providing transdermal communication with, and power to, a device implantable internal to the body of a patient, said system comprising:
   a) an external device;
   b) said internal device;
   c) a first ferromagnetic core;
   d) a second ferromagnetic core;
   e) first and second coils wound on the first ferromagnetic core and coupled to said external device;
   f) first and second coils wound on the second ferromagnetic core and coupled to said internal device;
      wherein the external and internal devices communicate in at least in one direction by means of inductive coupling between said first coil on said first core and said first coil on said second core and wherein power is transmitted from said external device to the internal device by means of inductive coupling between the second coil on said first core and second coil on said second core;
      said coils being constructed and arranged to minimize interference between said first coils and said second coils respectively.

2. A system according to claim 1 wherein the first and second coils on the first said core are wound substantially orthogonally to each other and similarly the first and second coils on the second said core are wound substantially orthogonally to each other so that when the cores are arranged in parallel the first coils are substantially parallel and the second coils are substantially parallel so that the inductive coupling between the said second coils is substantially independent of the inductive coupling between the said first coils.

3. A system according to claim 2 wherein the external device and the external core are integrated into a single housing.

4. A system according to claim 2 wherein said internal device and the internal core are integrated into a single housing.

5. A system according to any of claims 1 to 4 wherein said first coils operate at a first common frequency and said second coils operate at a second common frequency.

6. A system according to claim 3 wherein said housing is adapted to be placed behind the pinna.

7. A system according to claim 3 wherein said housing is adapted to be inserted into the ear canal.

8. A system according to claim 2 further including a cable, wherein said external device is adapted to be placed behind the pinna and said external coil is located within the ear canal, said external device and external coil being connected by said cable.

9. The system according to claim 1 wherein each of said cores comprises a cylindrical shape.

10. The system according to claim 1 wherein at least one of said cores comprises a rectangular prism.

11. The system according to claim 1 wherein said second core is shorter than said first core.

12. A system according to claim 1 wherein the cross section of said first core is of a different shape to the cross section of said second core.

13. A system according to claim 5 wherein said second common frequency is lower than said first common frequency.

14. A system according to claim 1 wherein at least one of the cores has a semi-circular cross section.

15. A system for providing transdermal communication with, and power to, a device implantable internal to the body of a patient, said system comprising:
   a) an external device;
   b) said internal device;
   c) a first ferromagnetic core;
   d) a second ferromagnetic core;
   e) first and second coils wound on the first ferromagnetic core and coupled to said external device;
   f) first and second coils wound on the second ferromagnetic core and coupled to said internal device;
      wherein the external and internal devices communicate in at least in one direction by means of inductive coupling between said first coil on said first core and said first coil on said second core and wherein power is transmitted from said external device to the internal device by means of inductive coupling between the second coil on said first core and second coil on said second core;
      each said first coils being oriented substantially orthogonally with respect to the corresponding second coils so that the inductive coupling between said first coils is independent of the inductive coupling of said second coils.

16. The system of claim 15 wherein said first coils operate at a first common frequency and wherein said second coils operate at a second common frequency.

17. The system of claim 15 wherein each of said cores comprises a cylindrical shape.

18. The system of claim 15 wherein at least one of said cores comprises a rectangular prism.

19. The system of claim 15 wherein said second core is shorter than said first core.

20. The system of claim 15 wherein at least one of said cores comprises a semicircular shape.

* * * * *